United States Patent [19]

Pollack

[11] Patent Number: 4,650,789

[45] Date of Patent: Mar. 17, 1987

[54] METHOD AND COMPOSITION FOR INCREASING PRODUCTION OF SEROTONIN

[75] Inventor: Robert L. Pollack, Philadelphia, Pa.

[73] Assignee: Commonwealth Medical Corporation of America, Allentown, Pa.

[21] Appl. No.: 787,502

[22] Filed: Oct. 15, 1985

[51] Int. Cl.$^4$ .................... A61K 31/40; A61K 31/44; A61K 31/62; A61K 31/70; A61K 31/435

[52] U.S. Cl. ..................................... 514/23; 514/161; 514/277; 514/356; 514/419

[58] Field of Search .................. 514/23, 277, 161, 419, 514/356

[56] References Cited

U.S. PATENT DOCUMENTS

| | | | |
|---|---|---|---|
| 3,172,809 | 3/1965 | Montandraud | 167/65 |
| 3,278,379 | 10/1966 | Mansor | 167/65 |
| 3,282,778 | 11/1966 | Lobel | 167/55 |
| 3,312,593 | 4/1967 | Sheen et al. | 167/65 |
| 3,698,912 | 10/1972 | Winitz | 99/14 |
| 4,210,637 | 7/1980 | Wurtman et al. | 424/180 |
| 4,472,387 | 9/1984 | Laruelle et al. | 424/180 |
| 4,482,567 | 11/1984 | Tamir et al. | 424/274 |
| 4,530,790 | 7/1985 | Monoghan et al. | 260/239.3 P |
| 4,551,471 | 11/1985 | De Luca et al. | 514/419 |

OTHER PUBLICATIONS

The Control of Brain Tryptophan Concentration, G. Curzon, Acta Vitamin. Enzymol., (Milano), 1975, pp. 69–71.

Mechanisms of Elevation of Rat Brain Tryptophan Concentration by Various Doses of Salicylate, A. A.-B. Badawy, Br. J. Pharmac., 1982, pp. 211–213.

The Effect of Sodium Salicylate on the Binding of L-Tryptophan to Serum Proteins, McArthur et al, J. Pharm. Pharmac., 1969, pp. 744–750.

The Effect of Tryptophan on Postoperative Endodontic Pain, Shpeen et al, Oral Surgery, Oral Medicine and Oral Pathology, vol. 58, 1984, pp. 446–449.

Tryptophan in the Treatment of Depression, Young et al, Adv. Exptl. Med. Biol., vol. 133, 1981, pp. 727–737.

How Foods Affect the Way You Feel, Good Housekeeping, "The Better Way", 1984, p. 222.

Primary Examiner—Stanley J. Friedman
Attorney, Agent, or Firm—Lawrence J. Shurupoff

[57] ABSTRACT

The production of the neurotransmitter serotonin is increased through administration of a therapeutic composition which includes L-tryptophan in combination with a salicylate, pyridoxine, niacin and a carbohydrate such as fructose. Both the absolute free fraction and the relative amount of the albumin-bound fraction of serum L-tryptophan are increased so that transport of L-tryptophan from the blood plasma across the blood-brain barrier into the brain is increased. Once within the brain, L-tryptophan is converted to serotonin.

16 Claims, No Drawings

METHOD AND COMPOSITION FOR INCREASING PRODUCTION OF SEROTONIN

CROSS-REFERENCE TO RELATED APPLICATION

Reference is made to the copending patent application of Robert L. Pollack and Lawrence Durst, Ser. No. 771,325, filed Aug. 30, 1985 and assigned to the same assignee as the assignee of the present application.

BACKGROUND OF THE INVENTION

1. Field of the Invention

This invention relates generally to a dietary therapeutic supplement for increasing the production or turnover of serotonin within the brain, thereby decreasing or eliminating pain, depression, and other undesirable physiological conditions. The invention particularly relates to a composition which promotes the transport of both bound and unbound tryptophan from the blood into the brain where tryptophan is converted into the neurotransmitter serotonin.

2. Description of Prior Developments

Attention has recently turned to nontraditional methods and compositions for treating various physiological disorders in an effort to provide relief in those instances where standard techniques have proven ineffective and where it is desired to avoid the drawbacks of conventional pharmaceuticals. More particularly, attention has turned to new methods and compositions for treatment of pain, depression, insomnia and appetite control.

One approach has been to attempt to relieve such conditions through dietary supplementation of L-tryptophan (tryptophan). Once within the brain, neurons convert tryptophan into the neurotransmitter serotonin. It has been found that an increase of tryptophan in the brain increases the brain's production of serotonin. The level of serotonin within the brain has been shown to be linked to sleep, appetite, depression and pain threshold. Disturbances in the brain causing reduced levels of serotonin have been linked to clinical depression, insomnia, and lowered pain threshold. The latter abnormality results in chronic, intractable pain.

It is known that dietary supplementation of tryptophan increases the level of tryptophan within blood plasma and facilitates the passage of tryptophan across the blood-brain barrier into the brain. The increased amount of tryptophan in the brain permits a greater amount of tryptophan to be converted to the neurotransmitter serotonin.

The level of one's pain threshold, a mechanism that normally prevents the brain from interpreting stimuli below a certain level as pain, is directly related to the amount of serotonin that is present in the brain. The higher the level of serotonin that is present, the higher will be the pain threshold level, up to a normal maximum level. With normal amounts of serotonin, one can function in a normal manner and not be subjected to myriad stimuli (such as from muscle activity) that could be interpreted as pain impulses. Moreover, clinical depression and insomnia can also be relieved by increasing serotonin production within the brain, up to a normal level.

In order for tryptophan to be converted to serotonin in the brain, it must cross a separating mechanism that exists between the blood vessels and the brain. To reach the brain, tryptophan requires a carrier transport mechanism which literally carries tryptophan across this very selective blood-brain barrier into the brain. Because of its polar nature, tryptophan requires a carrier protein to transport it across the blood-brain barrier. Not only is tryptophan carried by this transport mechanism, but other selected amino acids, called large electrically neutral amino acids (LNAAs), are carried as well. Tryptophan not only has to compete with these LNAAs for access to the transport carrier mechanism, it also has a lower affinity for the carrier system than does the LNAAs. To compound this biased situation further, tryptophan in foods is generally present in lower amounts than the LNAAs—particularly in animal proteins. All of these factors contribute to limit the amount of tryptophan that gets through to the brain, to be finally converted into serotonin.

There are numerous conditions, improper diet constitutes one of them, that can interfere with and decrease the amount of tryptophan that normally passes through the blood-brain barrier into the brain each day. This comes about when the ratio of tryptophan to LNAAs in the blood going to the brain is lower than normal. This means that the number of molecules of tryptophan present at the blood-brain barrier is much smaller than the number of LNAAs present at the same blood-brain barrier. The LNAAs outnumber and overwhelm the tryptophan by monopolizing most of the transport carriers. Accordingly, very little tryptophan is provided passage into the brain, compared to the number of LNAAs that are provided passage.

In attempting to correct this improper tryptophan/LNAA ratio, it was found that increasing the total protein intake (obtained from normal dietary sources) in order to add more tryptophan to the system paradoxically results in an even greater decrease in the pain threshold level. This is so because there are usually more LNAAs than there is tryptophan in food. Experimental studies have established the fact that increasing the amount of protein as food, in order to improve the tryptophan/LNAA ratio, only makes the tryptophan/LNAA ratio worse because of the greater intake of the LNAAs over the intake of the tryptophan.

With less tryptophan getting into the brain, less serotonin is formed, and the pain threshold is lowered to the point where low level sensory perceptions which would have been filtered out by the normal pain threshold level are now interpreted by the body as pain stimuli and are experienced as pain. This pain can span the gamut from relatively insignificant annoyances to chronic, unremitting, intractable, excrutiating pain. Because this type of pain stems from a biochemical imbalance involving the tryptophanserotonin relationship which cannot be corrected by any medication, it is unmanageable by any conventional drug therapy—because the drug does not address itself to the correction of this specific biochemical imbalance. The same is true in the case of clinical depression, insomnia and several appetite-related disorders. Conventional therapy for these conditions typically does not consider or correct a possible serotonin deficiency.

Accordingly, a need exists for a method and composition for transporting an effective dose of tryptophan across the blood-brain barrier into the brain and for promoting the conversion of tryptophan into serotonin in order to relieve pain, depression, insomnia and other undersirable physiological conditions.

SUMMARY OF THE INVENTION

The present invention has been designed as a dietary therapeutic composition including a combination of ingredients which will provide the proper and effective dietary supplementation of both free and albumin-bound tryptophan for increasing the production of serotonin in the brain up to a normal level. Increased serotonin production can decrease or eliminate chronic pain, particularly in those conditions where the pain stems from an unknown origin, and not due to any known medical, dental or psychological reason. Moreover, clinical depression, insomnia and appetite disorders may also be relieved or eliminated via such dietary supplementation.

The administration of pure tryptophan will: (1) help to improve the ratio of blood tryptophan to blood LNAAs, (2) help to increase the amount of tryptophan that will enter the brain, and (3) help to increase the serotonin level and raise the pain threshold level while concurrently relieving depression, insomnia and certain appetite-related disorders. The effectiveness of pure tryptophan in raising the pain threshold level and in relieving depression, insomnia and other disorders can be improved with the addition of other specific dietary supplements as set forth below.

The oral administration of tryptophan in combination with several other operative ingredients taken under proper dietary conditions can provide a supplementary intake of this particular amino acid which will correct an improper tryptophan/LNAA ratio so as to return the level of serotonin within the brain to a statistically normal level. The dietary supplementation of tryptophan, combined with a low fat, high carbohydrate and adjusted protein diet, results in a significant reduction in the pain intensity experienced by chronic pain patients and relieves or eliminates depression brought about by a deficiency of serotonin. Appetite can also be decreased in this manner.

A particularly effective composition has been found to include tryptophan, niacinamide, pyridoxine, and a salicylate such as acetylsalicylic acid (aspirin). A carbohydrate may also be added to this composition in the form of a sugar. If a carbohydrate is included, fructose is preferred since it yields a steadily metered release of insulin into the blood.

It is therefore an object of the invention to provide a method and composition for relieving pain, depression, insomnia and other disorders through dietary supplementation of tryptophan.

Another object is to efficiently transport tryptophan across the blood-brain barrier so that an effective pain, depression and insomnia-relieving quantity of tryptophan is converted in the brain to serotonin thereby raising serotonin to a normal level.

Still another object of the invention is to provide a method and composition for promoting the conversion of tryptophan to serotonin within the brain.

Yet another object is to provide a method and composition for relieving pain, depression and insomnia which triggers the release or displacement of tryptophan from its usual protein-bound or complexed state within the blood plasma to a free, unbound state in order to increase the free tryptophan concentration in blood.

A further object is to increase both the bound and unbound (or complexed) fraction of tryptophan within blood plasma in order to maximize the amount of tryptophan transported across the bloodbrain barrier into the brain for production of serotonin.

Various other objects, features and attendant advantages of the present invention will be more fully appreciated as the same becomes better understood from the following detailed description.

DETAILED DESCRIPTION OF THE PREFERRED EMBODIMENTS

L-tryptophan is usually not transported in the blood in a free state, but rather in a bound or complexed form with the protein albumin, a plasma component. In fact, L-tryptophan is the only circulating amino acid that is significantly bound to human serum albumin. It has been shown that various salicylates displace tryptophan from its protein binding site with albumin in blood plasma thereby raising the free or unbound tryptophan concentration in the blood. The bond-breaking effect exerted by salicylates on the binding of tryptophan to albumin causes a greater availability of free tryptophan molecules for diffusion into body cells.

In humans, the ingestion of aspirin causes a release of tryptophan from its binding site on serum albumin, and results in the presence of a free, unbound fraction of tryptophan within the blood. It has now been determined that it is primarily the free fraction of serum tryptophan which controls the concentration of brain tryptophan as well as the brain's production of serotonin.

The brain tryptophan level reflects brain serotonin turnover so that the resultant increase in the availability of circulating free tryptophan to the brain leads to an enhancement of brain serotonin synthesis. The amount of salicylate which significantly influences serotonin metabolism (synthesis) ranges from 0.06 gram to 0.3 gram.

There are four major operative ingredients which, when combined according to the invention, yield an effective composition for promoting the transport of tryptophan from the blood plasma into the brain. As noted above, once in the brain, tryptophan is converted to serotonin which has been shown to increase one's pain threshold level and to relieve depression and insomnia. In addition to the primary ingredient tryptophan, three additional ingredients are provided to facilitate tryptophan transport into the brain and/or to promote its conversion into serotonin.

Niacinamide is the first additional ingredient which promotes or facilitates tryptophan transport into the brain. Niacin is an essential nutrient that the human body must have at all times. Because of niacin's importance, the body has evolved a method by which it can synthesize niacin from tryptophan. More particularly, 60 milligrams of tryptophan is used by the body to make each milligram of niacin. Studies in humans have shown that the amount of niacin the body gets from tryptophan amounts to about one-half of the total amount of niacin that the body needs each day, that is, about 13–19 mg. This means that from $(13/2 \times 60)$ mg to $(19/2 \times 60)$ mg or 390 mg to 570 mg of tryptophan is needed each day for its conversion to niacin.

In order to attempt to minimize the destruction of the supplemental tryptophan within the body via synthesis into niacin, niacinamide or nicotinamide is included along with the tryptophan to provide the body with the pre-formed vitamin niacin.

The next operative ingredient of the invention is pyridoxine (vitamin $B_6$). Pyridoxine is essential in the tryptophan-serotonin conversion process and is part of the enzyme system which functions directly in the conversion of tryptophan to serotonin. By providing the body with this vitamin at the same time that the supplemental tryptophan is administered, this important nutrient will be provided to individuals whose dietary intake of this vitamin may have been deficient. This will ensure efficient and substantially complete conversion of tryptophan to serotonin.

Another major ingredient, but possibly the most important, is a salicylate such as acetylsalicylic acid (aspirin). As previously noted, tryptophan is usually not transported in the blood in a free state, but rather in a bound or complexed form with the protein albumin, a plasma component. Tryptophan is the only circulating amino acid that is significantly bound to human serum albumin. It has been shown that salicylates displace tryptophan from its protein binding site on albumin in blood plasma thereby raising the free, circulating tryptophan concentration in blood.

The "saturation" quantity or the smallest amount of acetylsalicylic acid with which the highest tryptophan-releasing effect has been attained is approximately 0.3 gram. The maximum bondbreaking or displacing effect of aspirin is directly proportional to quantities administered from 0.06 gram to 0.3 gram, but is generally not increased with greater amounts, although greater amounts could certainly be used.

To further promote the production of serotonin, a carbohydrate such as a sugar may be included in the composition for triggering the release of insulin. A preferred carbohydrate which may be added to any of the combinations is the monosaccharide sugar, fructose. Investigations have shown that dietary carbohydrate causes an increase in the relative concentration of blood tryptophan levels; i.e., the amount of tryptophan is increased relative to the amount of the interfering large neutral amino acids that compete with tryptophan for the transport carrier mechanism in the brain. Insulin, when elaborated into the blood stream in response to an increase in blood sugar concentration serves to drive amino acids into the body tissues while the blood courses on its way to the brain. The tryptophan-albumin complex is not affected by this insulin action, and thus remains available to reach the brain. Thus, this complex is not "lost" to the body tissues. However, the other amino acids are removed from the blood, thereby increasing the relative percentage of tryptophan in the blood. Carbohydrate intake, therefore, with its insulin-releasing action, helps to improve the albumin-bound tryptophan/LNAA ratio in favor of the tryptophan and increases the amount of tryptophan crossing the blood-brain barrier into the brain. Fructose may be included in each dosage (capsule) as a preferred source of carbohydrate to achieve this insulin/LNAA/tryptophan effect because of the even, steady, and uniform release of insulin effected by fructose as compared to other carbohydrates which trigger a sudden spike of insulin release.

While it may seem paradoxical to release tryptophan from its complexed state with albumin through administration of a salicylate, then to drive the resulting free tryptophan into the body tissues along with the other free amino acids via administration of a carbohydrate and release of insulin, the end result of this action is an overall increase in the transport of tryptophan into the brain. The exact interaction in this case is not completely known, although the combination of the free tryptophan provided by oral administration of the composition and the free tryptophan released from serum albumin may not collectively enter the body tissues under the influence of insulin to the extent or relative percent that the other free amino acids do, thereby increasing the relative serum concentration of free tryptophan.

Moreover, since not all of the serum tryptophan is released by the aspirin from its bound state, the remaining albumin-bound tryptophan is allowed to reach the brain at which point it is freed from albumin and transported into the brain by the body's own release mechanism. Thus, the combined effect of the administration of a salicylate and a carbohydrate along with free tryptophan is to increase both the absolute free fraction of circulating tryptophan and the relative amount of albumin bound tryptophan in relation to the remaining LNAAs.

It should be emphasized that aspirin is used according to the invention solely for its ability to safely break the bond between tryptophan and albumin in order to increase the free fraction of serum tryptophan and not for aspirin's well-known analgesic effect. In fact, aspirin administered alone in the dosages set forth below (without the additional ingredients) will not lower the threshold of pain to any degree near that when combined with tryptophan, niacin, pyridoxine and a carbohydrate such as fructose. Aspirin alone would not provide the required supplementation of tryptophan in those cases where tryptophan is deficient. Moreover, the 150 mg dosage of aspirin noted below is about ¼ that which is commonly used for aspirin's analgesic effect.

While aspirin is the pharmaceutical agent presently preferred to effect release of tryptophan from its bound or complexed state with albumin, any other pharmaceutically acceptable salicylate such as sodium salicylate or any other substance which safely produces this release would serve as well. For example, acetanilid, acetophenetidin, and aminopyrine could be used in about the same dosage as aspirin to achieve the same result. Other pharmaceutically acceptable substances have been found capable of releasing tryptophan from serum albumin and could be combined with tryptophan, niacin, pyridoxine and fructose in addition to or in place of a salicylate so as to fulfill the goal of the present invention. Such substances include helparin, isoprenaline, aminophylline, dopa, clofibrate, unesterified fatty acids, probenecid, bulbocapnine, and acetominophen.

While the weight of each ingredient listed below could vary up to approximately 50%, a preferred composition of the invention for a therapeutically and pharmacologically effective single (capsule) dosage for a typical patient is as follows:

1. L-tryptophan (one of the eight essential amino acids found in most protein foods) . . . 25 mg (5 parts by weight)
2. Niacinamide (Niacin or nicotinamide, a natural vitamin found in such foods as meat, whole grains, poultry, and fish) . . . 25 mg (1 part by weight)
3. Pyridoxine (Vitamin $B_6$, a natural vitamin found in such foods as meat, whole grains, poultry, and fish) . . . 25 mg (1 part by weight)
4. Fructose (a natural sugar found in such foods as fruits and honey) . . . 25 mg. (5 parts by weight)
5. Aspirin (acetylsalicylic acid) . . . 150 mg (6 parts by weight).

A patient may safely take one capsule by oral administration once an hour up to 2 capsules per day.

This dosage will effectively treat such maladies as insomnia, depression, lowered pain threshold, excessive appetite and multiple sclerosis.

While the primary goal of this invention is to relieve pain and depression, the composition may also be effective in the treatment of insomnia, the prevention of suicide, the curbing of appetite, and the treatment of multiple sclerosis.

Obviously, numerous modifications and variations of the present invention are possible in light of the above teachings. It is therefore to be understood that within the scope of the appended claims, the invention may be practiced otherwise than as specifically described herein.

What is claimed is:

1. A therapeutic method for treating physiological disorders resulting from a deficiency of L-tryptophan, wherein said method comprises:
   administering to a patient a dosage of a composition comprising L-tryptophan in an amount sufficient to increase transport of L-tryptophan into the patient's brain and acetylsalicylic acid in an amount sufficient to release L-tryptophan from the patient's serum albumin, said dosage of the composition being sufficient to increase production of serotonic within the patient's brain to a level which provides relief of said physiological disorders.

2. The method fo claim 1, which further comprises administering to the patient a dosage of a sugar, administering a dosage of a niacin supplement and administering a dosage of pyridoxine.

3. A therapeutic composition for increasing production of serotonic within a patient's brain, comprising:
   a dosage of at least 62.5 mg of L-tryptophan for increasing the transport of L-tryptophan into the patient's brain; and
   a dosage of at least 60 mg of acetylsalicylic acid for releasing L-tryptophan from the patient's serum albumen, said dosages combined so as to increase said production of serotonin to a level which provides relief of physiological disorders.

4. The composition of claim 3 further comprising at least 12.5 mg of a niacin supplement.

5. The composition of claim 3 further comprising at least 12.5 mg of pyridoxine.

6. The composition of claim 3 further comprising at least 62.5 mg of fructose.

7. The composition of claim 3, further comprising at least 12.5 mg of a niacin supplement, at least 12.5 mg of pyridoxine and at least 62.5 mg of fructose.

8. A therapeutic composition for increasing production of serotonin within a patient's brain, comprising a dosage of L-tryptophan in an amount sufficient to increase transport of L-tryptophan into the patient's brain and a dosage of acetylsalicylic acid in an amount sufficient to release L-tryptophan from the patient's serum albumen, said dosages combined so as to increase said production of serotonin to a level which provides relief of physiological disorders.

9. The composition of claim 8 further comprising at least 12.5 mg of a niacin supplement.

10. The composition of claim 8, further comprising at least 12.5 mg of pyridoxine.

11. The composition of claim 8, further comprising at least 62.5 mg of fructose.

12. The composition of claim 8, further comprising at least 62.5 mg of a sugar.

13. A therapeutic composition for increasing production of serotonic within a patient's brain, comprising:
   L-tryptophan in an amount ranging from 2.5 to 7.5 parts by weight; and
   acetylsalicylic acid in an amount ranging from 3 parts by weight to 9 parts by weight.

14. The composition of claim 13 further comprising a niacin supplement in an amount ranging from ½ part by weight to 1.5 parts by weight.

15. The composition of claim 13 further comprising pyridoxine in an amount ranging from ½ part by weight to 1.5 parts by weight.

16. The composition of claim 13 further comprising a sugar in an amount ranging from 2.5 parts by weight to 7.5 parts by weight.

* * * * *